United States Patent
Laurencin et al.

(10) Patent No.: US 9,757,132 B2
(45) Date of Patent: Sep. 12, 2017

(54) MECHANICALLY COMPETENT SCAFFOLD FOR ROTATOR CUFF AND TENDON AUGMENTATION

(75) Inventors: Cato T. Laurencin, Avon, CT (US); Mark T. Aronson, Midlothian, VA (US); Lakshmi Sreedharan Nair, Avon, CT (US); Joseph W. Reilly, Chatham, NJ (US)

(73) Assignee: Biorez, Inc., New Haven, CT (US)

( * ) Notice: Subject to any disclaimer, the term of this patent is extended or adjusted under 35 U.S.C. 154(b) by 628 days.

(21) Appl. No.: 12/730,965

(22) Filed: Mar. 24, 2010

(65) Prior Publication Data
US 2011/0238179 A1 Sep. 29, 2011

(51) Int. Cl.
*A61F 2/08* (2006.01)
*A61B 17/11* (2006.01)
*D04C 1/02* (2006.01)

(52) U.S. Cl.
CPC ............ *A61B 17/1146* (2013.01); *A61F 2/08* (2013.01); *D04C 1/02* (2013.01); *D10B 2509/00* (2013.01)

(58) Field of Classification Search
CPC .... A61F 2/08; A61F 2/40; A61F 2310/00005; A61B 17/1714
USPC ................. 623/13.11–13.2; 264/103
See application file for complete search history.

(56) References Cited

U.S. PATENT DOCUMENTS

| | | |
|---|---|---|
| 3,797,047 A | 3/1974 | Pillet |
| 3,973,277 A * | 8/1976 | Semple et al. ............. 623/13.14 |
| 4,187,558 A | 2/1980 | Dahlen et al. |
| 4,483,023 A | 11/1984 | Hoffman, Jr. et al. |
| 4,610,688 A | 9/1986 | Silvestrini et al. |
| 4,728,329 A | 3/1988 | Mansat |
| 4,792,336 A | 12/1988 | Hlavacek et al. |
| 4,834,755 A | 5/1989 | Silvestrini |
| 4,917,699 A | 4/1990 | Chervitz |
| 4,979,956 A * | 12/1990 | Silvestrini .................. 623/13.11 |
| 4,987,665 A | 1/1991 | Dumican |
| 5,061,283 A | 10/1991 | Silvestrini |

(Continued)

FOREIGN PATENT DOCUMENTS

| | | |
|---|---|---|
| EP | 0122744 | 10/1984 |
| EP | 0334045 | 9/1989 |

(Continued)

OTHER PUBLICATIONS

Aoki, et al., "Transfer of latissimus dorsi for irreparable rotator-cuff tears.", *J. Bone Joint Surg. Br.*, 78(5):761-766 (1996).
Bellincampi, et al., "Viability of fibroblast-seeded ligament analogs after autogenous implantation.", J. Orthop. Res., 16:414-420 (1998).

(Continued)

*Primary Examiner* — Brian Pellegrino
(74) *Attorney, Agent, or Firm* — Pabst Patent Group LLP

(57) ABSTRACT

A device has been developed to augment the rotator cuff tendon tissue as it proceeds in healing. The device has two purposes: to provide initial stability to the rotator cuff repair site to allow early mobilization of the upper extremity of the patient, and to allow for reinforcement of rotator cuff tendon repairs to increase the likelihood of successful rotator cuff tendon repairs. The device consists of an inter-connected, open pore structure that enables even and random distribution and in-growth of tendon cells. The braided structure allows for distribution of mechanical forces over a larger area of tissue at the fixation point(s).

18 Claims, 1 Drawing Sheet

(56) References Cited

U.S. PATENT DOCUMENTS

| | | | |
|---|---|---|---|
| 5,263,984 | A | 11/1993 | Li et al. |
| 5,980,564 | A | 11/1999 | Stinson |
| 6,375,662 | B1 * | 4/2002 | Schmitt .................. 606/151 |
| 6,458,148 | B1 | 10/2002 | Dauner |
| 6,669,706 | B2 | 12/2003 | Schmitt |
| 8,486,143 | B2 * | 7/2013 | Laurencin et al. ........ 623/13.14 |
| 8,758,437 | B2 * | 6/2014 | Laurencin et al. ........ 623/13.14 |
| 2002/0133229 | A1 * | 9/2002 | Laurencin et al. ........ 623/13.17 |
| 2004/0059416 | A1 | 3/2004 | Murray et al. |
| 2006/0141012 | A1 | 6/2006 | Gingras |
| 2007/0156237 | A1 * | 7/2007 | Kwak .................. 623/13.14 |
| 2007/0233242 | A1 | 10/2007 | Laurencin |
| 2008/0031923 | A1 | 2/2008 | Murray et al. |
| 2008/0051888 | A1 | 2/2008 | Ratcliffe et al. |
| 2008/0161917 | A1 | 7/2008 | Koob |
| 2008/0215150 | A1 * | 9/2008 | Koob et al. ............ 623/13.14 |
| 2009/0024162 | A1 | 1/2009 | Shalaby |
| 2010/0016889 | A1 * | 1/2010 | Ferree .................. 606/228 |
| 2010/0161054 | A1 * | 6/2010 | Park et al. ............ 623/13.14 |
| 2010/0298937 | A1 * | 11/2010 | Laurencin et al. ........ 623/13.14 |
| 2011/0238179 | A1 | 9/2011 | Laurencin |
| 2012/0185041 | A1 | 7/2012 | Mortarino |

FOREIGN PATENT DOCUMENTS

| | | | |
|---|---|---|---|
| EP | 1177800 | 2/2002 | |
| EP | 1410810 | 4/2004 | |
| EP | 1493404 | 1/2005 | |
| WO | 9415550 | 7/1994 | |
| WO | 9527449 | 10/1995 | |
| WO | 9745147 | 2/1997 | |
| WO | 0172241 | 10/2001 | |
| WO | WO 2007/087353 | 8/2007 | |
| WO | 2004080346 | 1/2009 | |
| WO | WO 2009113076 A1 * | 9/2009 | ............... A61F 2/08 |

OTHER PUBLICATIONS

Bungaro, et al., "Comparative and experimental study on different tendinous grasping techniques in rotator cuff repair: a new reinforced stitch.", *Chir. Organi. Mov.*, 90(2):113-119 (2005).

Friedman, et al., "Autogeneic anterior cruciate ligament (ACL) anterior reconstruction of the knee. A review.", *Clin. Orthop. Relat. Res.*, 196:9-14 (1985).

Gazdag, et al., "Alternatives to Autogenous Bone Graft: Efficacy and Indications.", *J. Am. Acad. Orthop. Surg.*, 3(1):1-8 (1995).

Gerber, "Latissimus dorsi transfer for the treatment of irreparable tears of the rotator cuff.", *Clin. Orthop. Relat. Res.*, 275:152-160 (1992).

Goulet, et al., "Tendons and Ligaments," Principles of Tissue Engineering (Lanza, Langer, and Chick, eds.), R. G. Landes Company and Academic Press, Inc., p. 639-645 (199.

Jackson, et al., "Intraarticular reaction associated with the use of freeze-dried, ethylene oxide-sterilized bone-patella tendon-bone allografts in the reconstruction of the anterior cruciate ligament", *Am. J. Sports Med.*, 18(1):1-10 (1990).

Jackson, et al., "Biologic and synthetic implants to replace the anterior cruciate ligament," *Arthroscopy*, 10:442-452 (1994).

Kimura, et al., "Reconstruction of a defect of the rotator cuff with polytetrafluoroethylene felt graft. Recovery of tensile strength and histocompatibility in an animal model", *J. Bone Joint Surg. Br.*, 85(2):282-287 (2003).

Koh, et al., "Supplementation of rotator cuff repair with a bioresorbable scaffold", *Am J Sports Med.*, 30(3):410-413 (2002).

Langer and Vacanti, "Tissue engineering", *Science*, 260(5110):920-926 (1993).

Shino, et al., "Maturation of allograft tendons transplanted into the knee. An arthroscopic and histological study", *J. Bone Joint Surg. Br.*, 70(4):556-660(1988).

International Search Report and Written Opinion for PCT Application PCT/US2014/023424 mailed Mar. 3, 2014.

\* cited by examiner

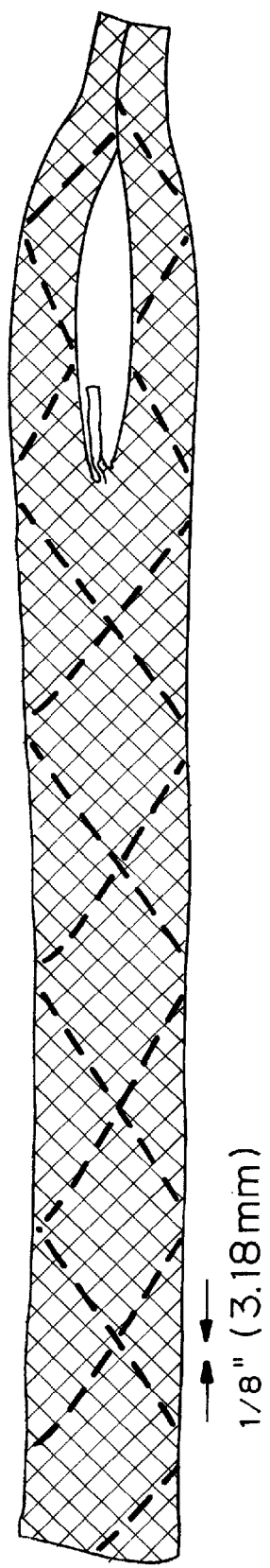

MECHANICALLY COMPETENT SCAFFOLD FOR ROTATOR CUFF AND TENDON AUGMENTATION

FIELD OF THE INVENTION

The present invention is in the field of implantable medical devices and prosthesis, particularly, devices useful as both a structural prosthetic for articular tissue and an in vivo scaffold for the regeneration of articular tissue, including tendons for rotator cuff repair, and methods of making and using the devices.

BACKGROUND OF THE INVENTION

Proper functioning of the human shoulder is in part governed by the rotator cuff muscles. These muscles originate from scapula (one of the three shoulder bones) and attach to the humerus via fibrous tendons as they approach the outer aspect of the shoulder thereby surrounding the anterior, superior and posterior of the shoulder joint. The motion of the shoulder is facilitated by the contraction of rotator cuff muscles which pull the rotator cuff tendons. Thus the rotator cuff allows movement of the upper arm for activities such as reaching and throwing.

Disorders of the rotator cuff, particularly tears of the rotator cuff tendons, can cause significant shoulder pain and disability. Young athletes, middle-aged workers, and a substantial portion of the elderly population can suffer a rotator cuff injury which prevents them from working, playing sports, enjoying hobbies or performing routine daily activities. Active people, including athletes, are highly susceptible to rotator cuff problems, particularly as they get older. It has been estimated that more than 100,000 rotator cuff surgeries are performed in the United States each year. Rotator cuff lesions are one of the most common causes of upper extremity disability.

A serious concern with a rotator cuff tear is that the rotator cuff has limited healing potential after tears. The non-surgical treatment for rotator cuff tears includes some combination of anti-inflammatory medication, limiting overhead activity, steroid injections, and strengthening exercises often in association with physical therapy. Surgery to repair the rotator cuff is often advised when a rotator-cuff tear causes severe shoulder weakness or when there has been no improvement following non-surgical treatment. Repair of a torn rotator cuff generally consists of reapproximating the tendon edge to a bony trough through the cortical surface of the greater tuberosity.

Traditionally, surgeons use suture and suture anchors to repair weak, frayed and damaged tissue. Several surgical procedures have been performed to cover massive irreparable rotator cuff tears, including tendon transfer, tendon mobilization and tendon autografts patch grafts using biological or synthetic materials [Aoki et al., 1996 *J Bone Joint Surg Br.* 1996 September; 78(5):761-6; Gerber 1992 Clin Orthop Relat Res. 1992 February; (275):152-60; Kimura et al., 2003 *J Bone Joint Surg Br.* 2003 March; 85(2):282-7]. Suture anchors were found to be useful in rotator cuff repair because they could be placed with less surgical dissection and allowed for the "mini-open" technique to become popularized. There are two major disadvantages to using bioresorbable suture anchors that are currently available and used in arthroscopic rotator cuff repair. Passing the suture through the rotator cuff can often be challenging due to the limited amount of working area in the subacromial space. While knots can be tied arthroscopically in a secure fashion, the process is very time-consuming and clearly has a long learning curve. Arthroscopic repair has been suggested for rotator cuff repair, however is burdened by a percentage of recurrences that is greater than the repair carried out when an open technique is used [Bungaro et al., 2005 Chir Organi Mov. 2005 April-June; 90(2):113-9]. It has been found that when an open technique is used, good hold can be guaranteed by using reinforced stitches such as the modified Mason-Allen suture.

The clinical results of all current rotator cuff repair techniques are often sub-optimal and often pre-injury functional levels are not obtained. Augmentation devices have not provided a satisfactory alternative. Several factors limit the extensive use of biological grafts including donor site morbidity, limited availability of autografts material the risk of disease transmission from allografts and patch grafts become mechanically weaker over time as they cause adverse reactions. Extracellular matrices are widely employed by sports-medicine and orthopedic surgeons for augmenting the torn rotator cuff and are intended to strengthen the tendon and enhance biological healing. More recently, synthetic bioabsorbable meshes have been commercialized for repair of soft tissues, including the rotator cuff.

Several extracellular matrix products (ECMs) are commercially available and include GraftJacket (Wright Medical Technology), CuffPatch (Organogenesis, licensed to Arthrotek), Restore (Depuy), Zimmer Collagen Repair (Permacol) patch (licensed by Tissue Science Laboratories), TissueMend (TEI Biosciences, licensed to Stryker), Ortho-ADAPT (Pegasus Biologics), and BioBlanket (Kensey Nash). These products are fabricated from human, cow, or pig skin, equine pericardium, human fascia latta, or porcine small intestine submuccosa. The manufacturers use various methods of decellularization, cross-linking, and sterilization; the end products possess varying properties of strength, stiffness, and suture-failure load. While there are many products available and many thousands of rotator cuff repairs being performed annually with extracellular matrices, little is known about clinical outcomes. One published study by Iannofti et al found that porcine small intestine mucosa (DePuy's Restore patch) did not improve the rate of tendon-healing or the clinical outcome scores of patients with massive and chronic rotator cuff tears. The relatively low resistance to suture pull-out and potential for immunological response (perceived or real) of ECMs has limited widespread use of ECMs for rotator cuff repair.

Depuy Orthopedics Inc, Warsaw, Ind. has developed SIS (intenstinal submucosa) for augmentation of rotator cuff tendon tears. The SIS materials have sold well, but have the disadvantage of originating from a contaminated animal source, necessitating a variety of cleaning steps. Some patients have sustained swelling, and what appears to be a graft versus host reaction to the SIS Material. GraftJacket is a product by Wright medical using cross banked human cadaver skin. While response levels are lower with this product, the material is very poorly degradable.

Some of the recent studies have indicated some advantages of using synthetic augmentation devices to support the healing of torn rotator cuff. Two synthetic, bioabsorbable products were recently 510 k cleared by the FDA, and both indications for use statements include rotator cuff repair. One of these products is SportMesh (marketed by Biomet) which is made from woven Artelon fibers. Artelon is a biodegradable poly(urethaneurea) material. SportMesh is currently under evaluation for treatment of rotator cuff tears at one or more US-based centers. A second synthetic product recently cleared by the FDA is the X-Repair (marketed by Synthasome) which is made from woven bioabsorbable poly(L-lactic acid) (PLLA) fibers. The X-Repair product was evaluated in a canine model and found to improve biomechanical function at 12 weeks. Another product of interest that was cleared by the FDA is Serica's SeriScaffold, a long-term bioabsorbable woven mesh of silk fibers. Two PLLA devices have been evaluated for rotator cuff repair; one study in sheep reported in 2000 showed a 25% increase in strength of the repair and a second study in goats reported in 2006 showed no significant difference in load to failure of the repair. One study by Koh et al. demonstrated the better biomechanical performance of damaged rotator cuff tendon while healing when the tear was augmented with woven polylactic acid structures [Koh et al., 2002 *Am J Sports Med.* 2002 May-June; 30(3):410-3]. See, for example, U.S. published application 2008/0051888.

There is a need for an alternative strategy to develop an augmentation device for rotator cuff repair and regeneration due to several reasons. First it has recently been found that up to 60 percent of rotator cuff tendon repairs are failing after repair, even in the hands of good surgeons. While some patients do well after surgery even with the re-torn rotator cuff tear, many do not, and in fact a re-torn rotator cuff is a negative predictor of outcome for a patient. Second, is the fact that traditional outcomes of rotator cuff repair are limited by biology. It takes four weeks to heal a rotator cuff repair, during which patients are not allowed to have significant mobilization of the shoulder. However, the decreased mobility of the joint can lead to significant shoulder stiffness which is a serious disadvantage. This clearly shows the importance of an augmentation device that would allow shoulder mobility while healing. Third, often there are gap areas that cannot be closed with rotator cuff tears. An augmentation device when employed could satisfactorily address this concern.

It is an object of the present invention to provide a biocompatible device for augmentation and repair of rotator cuff injuries.

It is still another object of the present invention to provide a method for producing a device for repair or augmentation of rotator cuff injury which results in improved strength retention and ingrowth of new tissue.

SUMMARY OF THE INVENTION

A braided rather than woven device has been developed to augment the rotator cuff tendon tissue as it proceeds in healing. The device has two purposes: to provide initial stability to the rotator cuff repair site to allow early mobilization of the upper extremity of the patient, and to allow for reinforcement of rotator cuff tendon repairs to increase the likelihood of successful rotator cuff tendon repairs. The device consists of an inter-connected, open pore structure that enables even and random distribution and in-growth of tendon cells. The braided structure allows for distribution of mechanical forces over a larger area of tissue at the fixation point(s).

The device can be formed of a degradable polymer. The degradable material is designed to degrade after a period of about nine to twelve months, to allow for repair or augmentation of the tendon prior to the device losing the structural and mechanical support provided by the degradable material.

The device is manufactured using 3-D braiding to create the proper porosity for tendon cell ingrowth and in conjunction with the degradable polymer, provides augmentation strength.

The device is implanted at the site of injury preferably during open surgery although it may be possible to implant arthroscopically, by securing the device using interference screws, rivets, or other attachment devices such as sutures. Torn or damaged tendons, or allograft tissue, may be sutured to or placed adjacent to the device to enhance healing or augmentation.

BRIEF DESCRIPTION OF THE DRAWING

FIG. 1 is a perspective view of a three dimensional (3-D) braid prepared using standard 3-D braiding techniques with final dimensions of 12 mm wide, 0.8 mm thick, cut to length.

DETAILED DESCRIPTION OF THE INVENTION

When developing an augmentation device, a bioresorbable device is highly preferred as it could prevent the need for a second surgery and at the same time significantly prevent long term biocompatibility issues found with permanent metallic, ceramic or polymeric implants.

The resorbable augmentation device needs to closely mimic the biomechanical properties of the tissue to be regenerated for a short span of time during the new tissue formation, until the regenerated tissue could satisfactorily perform the required functions. In addition to these requirements the resorbable augmentation device should present a favorable structure for cell infiltration and matrix deposition for neo-tissue formation. These facts points to the need for the development of a temporary augmentation device that closely mimics the structural features of the native tissue.

I. Tendon Rotator Cuff Augmentation Device

A polymeric fibrous structure that exhibits similar mechanical properties of human fibrous soft tissue, such as tendon, and is fabricated using standard 3-D braiding techniques. The mechanical properties of soft tissue and/or the fibrous structures can be determined by the placing a sample in a spring loaded clamp attached to the mechanical testing device and subjecting the sample to constant rate extension (5 mm/min) while measuring load and displacement and recording the resulting strain-stress curve. In particularly useful embodiments, the polymeric braided structure exhibits a stiffness in the range of stiffness exhibited by fibrous soft tissue. Typically, suitable stiffness will be in the range of about 10 to about 500 Newtons per millimeter (N/mm), and suitable tensile strength will be in the range of about 20 to about 1000 Newtons (N). In some embodiments, the stiffness of the polymeric fibrous structure will be in the range of about 20 to about 80 N/mm. The fibrous structure can be prepared using standard techniques for making a 3-D braided structure. The width and length dimensions of the device can vary within those ranges conventionally used for a specific application and delivery device. For example, dimensions of about 10 mm by 10 mm to about 100 mm by 100 mm. The device can be dimensioned to allow it to be rolled or otherwise folded to fit within a cannula having a small diameter to allow arthroscopic or laparoscopic implantation, fitting within openings on the order of about 0.5 mm to about 10 mm. In some embodiments, the fibrous structure defines openings on the order of about 0.5 mm to about 10 mm. In certain embodiments, the fibrous structure is braided using multifilament PLLA fibers that are plied to create a yarn bundle. Each 60 to 100 denier PLLA fiber is made up of 20-40 individual filaments. In particularly useful embodiments, the 3-D braided fibrous structure includes about twenty four 75 denier PLLA fibers made up of 30 individual filaments. The diameter of a 75 denier PLLA fiber is about 80-100 microns while the diameter of an individual filament is about 15-20 microns. In some embodiments, the fibers have a diameter ranging from about 50 microns to about 150 microns. In particularly useful embodiments, the fibers have a diameter ranging from about 80 microns to about 100 microns. In one embodiment, the device is formed using a braiding mechanism with 75 denier degradable polymer such as PLLA, having a relaxed width of between 10 mm and 14 mm and tensioned width of between 8 mm and 12 mm; relaxed thickness of between 0.8 mm and 1.2 mm and a tensioned thickness of between 0.6 mm 1.0 mm.

The braided structure can be packaged and sterilized in accordance with any of the techniques within the purview of those skilled in the art. The package in which the implant or plurality of implants are maintained in sterile condition until use can take a variety of forms known to the art. The packaging material itself can be bacteria and fluid or vapor impermeable, such as film, sheet, or tube, polyethylene, polypropylene, poly(vinylchloride), and poly(ethylene terephthalate), with seams, joints, and seals made by conventional techniques, such as, for example, heat sealing and adhesive bonding. Examples of heat sealing include sealing through use of heated rollers, sealing through use of heated bars, radio frequency sealing, and ultrasonic sealing. Peelable seals based on pressure sensitive adhesives may also be used.

The braided structures described herein can be used to repair, support, and/or reconstruct fibrous soft issue. The braided structures may rapidly restore mechanical functionality to the fibrous soft tissue. The braided structures may be implanted using conventional surgical or laparoscopic/arthroscopic techniques. The braided structure can be affixed to the soft tissue or to bone adjacent to or associated with the soft tissue to be repaired. In particularly useful embodiments, the braided structure is affixed to muscle, bone, ligament, tendon, to or fragments thereof. Affixing the braided structure can be achieved using techniques within the purview of those skilled in the art using, for example, sutures, staples and the like, with or without the use of appropriate anchors, pledgets, etc.

A. Polymeric Materials

Suitable degradable polymers include polyhydroxy acids such as polylactic and polyglycolic acids and copolymers thereof, polyanhydrides, polyorthoesters, polyphosphazenes, polycaprolactones, biodegradable polyurethanes, polyanhydride-co-imides, polypropylene fumarates, polydiaxonane polycaprolactone, and polyhydroxyalkanoates such as poly4-hydroxy butyrate, and/or combinations of these. Natural biodegradable polymers such as proteins and polysaccharides, for example, extracellular matrix components, hyaluronic acids, alginates, collagen, fibrin, polysaccharide, celluloses, silk, or chitosan, may also be used.

Preferred biodegradable polymers are lactic acid polymers such as poly(L-lactic acid) (PLLA), poly(lactic acid) (PLA), and poly(lactic-co-glycolic acid) (PLGA). The co-monomer (lactide-glycolide) ratios of the poly(lactic-co-glycolic acid) are preferably between 100:0 and 50:50. Most preferably, the co-monomer ratios are between 85:15 (PLGA 85:15) and 50:50 (PLGA 50:50). Blends of PLLA with PLGA, preferably PLGA 85:15 and PLGA 50:50 can also be used. The preferred polymer for the non-degradable region is a polyester and the preferred polymer for the degradable region is PLLA.

Material may be applied to the fibers to increase adhesion or biocompatibility, for example, extracellular matrix molecules such as fibronectin and laminin, growth factors such as EGF, FGF, PDGF, BMP, and VEGF, hyaluronic acid, collagens, and glycosaminoglycans.

B. Cell Seeding

The devices can optionally be seeded with cells, preferably mammalian cells, more preferably human cells. Alternatively, they are implanted and cells may attach to and proliferate on and within the devices. Various cell types can be used for seeding. In a preferred embodiment, for ligament and tendon replacement, the cells are either mesenchymal in origin or capable of generating mesenchymal cells. Accordingly, preferred cell types are those of the connective tissue, as well as multipotent or pluripotent adult or embryonic stem cells, preferably pluripotent stem cells. However, the scaffolds can be seeded with any cell type which exhibits attachment and ingrowth and is suitable for the intended purpose of the braided scaffold. Some exemplary cell types which can be seeded into these scaffolds when used for repair, regeneration or augmentation of connective tissue or other tissue types such as parenchymal tissues, include, but are not limited to, osteoblast and osteoblast-like cells, endocrine cells, fibroblasts, endothelial cells, genitourinary cells, lymphatic vessel cells, pancreatic islet cells, hepatocytes, muscle cells, intestinal cells, kidney cells, blood vessel cells, thyroid cells, parathyroid cells, cells of the adrenal-hypothalamic pituitary axis, bile duct cells, ovarian or testicular cells, salivary secretory cells, renal cells, chondrocytes, epithelial cells, nerve cells and progenitor cells such as myoblast or stem cells, particularly pluripotent stem cells.

Cells that could be used can be first harvested, grown and passaged in tissue cultures. The cultured cells are then seeded onto the three dimensional braided scaffold to produce a graft material composed of living cells and a degradable matrix. This graft material can then be surgically implanted into a patient at the site of ligament or tendon injury to promote healing and repair of the damaged ligament or tendon.

Growth factors and other bioactive agents may be added to the graft material. In a preferred embodiment, these include fibroblast growth factor (FGF), vascular endothelial growth factor (VEGF), epidermal growth factor (EGF), and bone morphogenic proteins (BMPs). Adhesive materials such as fibronectin and vimentin can also be added. These are preferably added in amount ranging from 0.1 nanogram to 1 micrograms. Cell isolates (for example, from marrow cells) or biological factors isolated from blood can also be added to the graft or placed with the graft.

II. Methods of Manufacture

The device is prepared using standard 3-D braiding techniques and equipment. The device is 3-D braided so that the structure has the desired combination of the fiber properties and porosity resulting from the 3-D braided structure The geometric parameters which determine the shape and fiber architecture of three-dimensional braids includes braiding angle distribution, fiber volume fraction, number of carriers, and braiding width. The braiding pattern can depend on braiding machinery/technique used. The device peak load strength range is from 20 to 1000 N, with an initial stiffness range of 20 to 500 N/mm. The devices are typically provided in a sterile kit, such as a foil or TYVEX® package.

III. Methods of Use

The device is used for repair or augmentation of articular injury, by implanting the device at a site in need of articular repair or augmentation.

In use, the devices are implanted to match the biomechanical properties of the tissue being repaired. This permits an early return to normal function post-operatively. The implanted device bears applied loads and tissue in-growth commences. The mechanical properties of the biodegradable material of the implant slowly decay following implantation, to permit a gradual transfer of load to the ingrown fibrous tissue. In a preferred embodiment, the degradation of the biodegradable material occurs after about 9-12 months. Additional in-growth continues into the space provided by the biodegradable material of the implant as it is absorbed. This process continues until the biodegradable material is completely absorbed and only the newly formed tissue remains.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A device for repair or augmentation of rotator cuff tissue comprising
   A three dimensional braided scaffold consisting of polymeric fibers plied to create multifilament yarn bundles, wherein the yarn bundles are braided to form the scaffold, wherein the polymeric fibers are degradable polymers selected from the group consisting of poly (L-lactic acid) or (PLLA), poly(lactic acid) or (PLA), poly(lactic-co-glycolic acid) or (PLGA), polyhydroxyalkanoates and silk, wherein the polymeric fibers which form the yarn bundles have a diameter between 50-150 microns,
   the scaffold forming an inter-connected, open pore structure that enables even and random distribution and in-growth of tendon cells and which provides structural and mechanical support for a period of about nine to twelve months following implantation and attachment at a site in or adjacent to the rotator cuff of an individual in need thereof,
   the scaffold comprising fixation point(s) to affix the scaffold to the soft tissue or to bone adjacent to or associated with the rotator cuff soft tissue to be repaired, wherein the scaffold has a length between 10 mm and 100 mm and width between 10 mm and 100 mm,
   wherein the scaffold distributes mechanical forces across and lengthwise over the tissue at the fixation point(s) and allows shoulder mobility while healing, and has an initial stiffness between 20 and 500 N/mm at the time of implantation.

2. The device of claim 1 having a peak load strength between 20 and 1000 N.

3. The device of claim 1 having a porosity between 50% and 70%, and pore size between 177 µm and 250 µm.

4. The device of claim 2 with an initial stiffness between 20 and 80 N/mm.

5. The device of claim 1, wherein the device is seeded with cells, ingrowth of which is supported by the scaffold.

6. The device of claim 5 wherein the cells are selected from the group consisting of mesenchymal cells, cells generating mesenchymal cells, fibroblasts, pluripotent stem cells, and multipotent stem cells.

7. A method for repairing or augmenting a damaged rotator cuff tendon or ligament in a patient comprising implanting at a site of a damaged tendon or ligament the device of claim 1 for repair or augmentation of rotator cuff tissue.

8. The method of claim 7 wherein the device has a peak load strength between 20 and 1000 N.

9. The method of claim 7 wherein the device has a porosity between 50% and 70%, and pore size between 177 µm and 250 µm.

10. The method of claim 8 wherein the device has an initial stiffness range between 20 and 80 N/mm.

11. The method of claim 7, wherein the device is seeded with cells, ingrowth of which is supported by the scaffold.

12. The method of claim 11 wherein the cells are selected from the group consisting of mesenchymal cells, cells generating mesenchymal cells, fibroblasts, pluripotent stem cells, and multipotent stem cells.

13. The method of claim 7 wherein the three dimensional braided scaffold is formed by braiding yarn bundles of plied multifilament polymeric fibers.

14. The method of claim 13 wherein the scaffold is braided from yarn bundles containing 60-100 denier multifilament polymeric fibers, wherein the multifilament polymeric fibers are plied from 20 to 40 polymer filaments.

15. A kit comprising the device for repair or augmentation of rotator cuff tissue of claim 1 and means for attachment.

16. The device of claim 1 wherein the scaffold is braided from yarn bundles containing 60-100 denier multifilament polymeric fibers, wherein the multifilament polymeric fibers are plied from 20 to 40 polymer filaments.

17. The device of claim 1 wherein the scaffold is formed by braiding multifilament polylactide fibers having a denier between 60-100.

18. The device of claim 17 wherein the scaffold is formed of 75 denier poly-L-lactide multifilament fibers.

* * * * *